United States Patent [19]

Emanuel et al.

[11] Patent Number: 4,486,440

[45] Date of Patent: Dec. 4, 1984

[54] RETINOPROTECTOR FOR TREATING INTRAOCULAR HEMORRHAGE, MYOPIC, CHORIORETINAL DYSTROPHIES, CONGENITAL RETINAL DYSTROPHIES, RETINAL BURNS AND PREVENTION OF INJURY IN LASERCOAGULATION

[75] Inventors: Nikolai M. Emanuel; Anna A. Shvedova; Leonid D. Smirnov; Larisa V. Spirina; Lev A. Katsnelson, all of Moscow, U.S.S.R.

[73] Assignees: Institut Khimicheskoi Fiziki; Institut Glaznykh Boleznei Imeni Gelmgoltsa; Vsesojuzny Nauchno-Issledovatelsky Khimiko-Farmatsevtichesky Institut, all of Moscow, U.S.S.R.

[21] Appl. No.: 523,954

[22] Filed: Aug. 17, 1983

[51] Int. Cl.³ .............................................. A61K 31/44
[52] U.S. Cl. .................................................. 424/263
[58] Field of Search ............................... 424/263, 267

[56] References Cited

U.S. PATENT DOCUMENTS 3,983,238  9/1976  Morisawa et al. .................. 424/263

OTHER PUBLICATIONS

Chem. Abst. 78, 84602(u) and 71256j, (1973)—Brown et al.

*Primary Examiner*—Douglas W. Robinson
*Attorney, Agent, or Firm*—Burgess, Ryan & Wayne

[57] ABSTRACT

This invention pertains to the field of medicine. A new medicinal drug, -retinoprotector for treating intraocular hemorrhage, myopic chorioretinal dystrophies, congenital retinal dystrophies, retinal burns and prevention of injury in lasercoagulation comprising the active substance 2-ethyl-6-methyl-3-hydroxypyridine hydrochloride having the following formula:

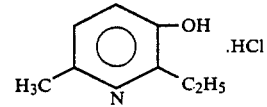

and a pharmaceutical diluent.

6 Claims, 6 Drawing Figures

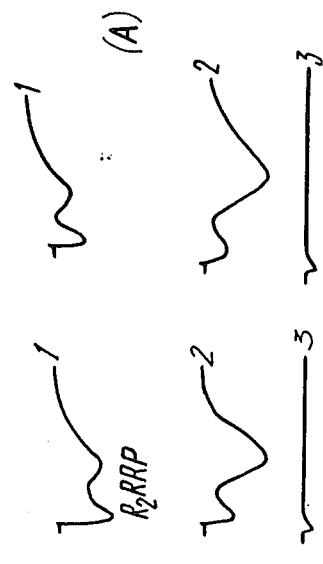
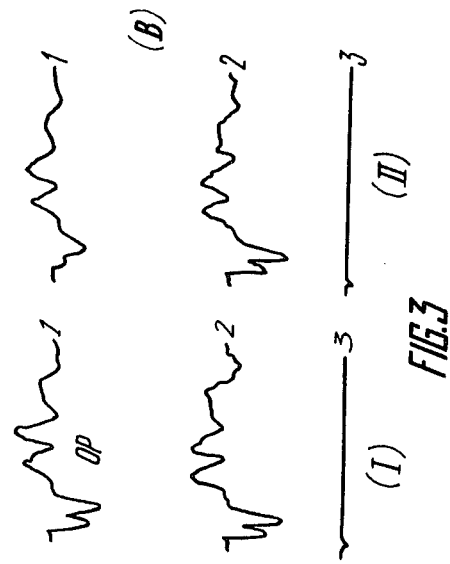
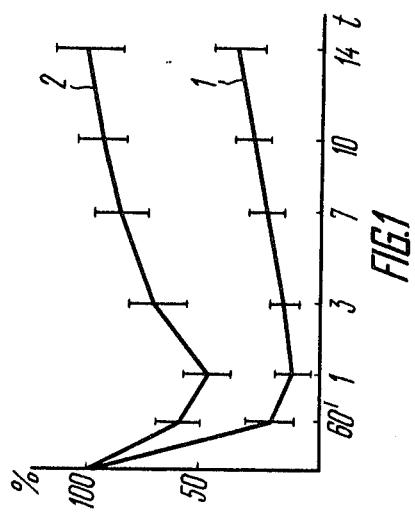
FIG.1
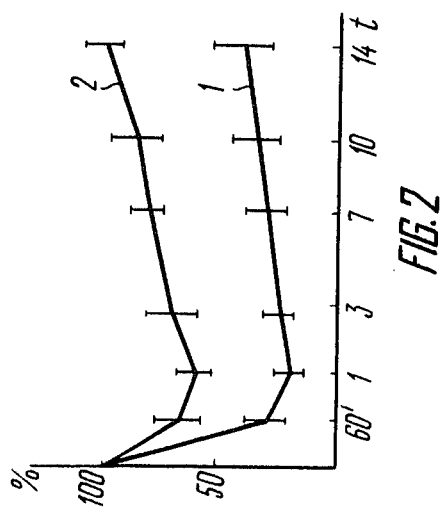
FIG.2

RETINOPROTECTOR FOR TREATING INTRAOCULAR HEMORRHAGE, MYOPIC, CHORIORETINAL DYSTROPHIES, CONGENITAL RETINAL DYSTROPHIES, RETINAL BURNS AND PREVENTION OF INJURY IN LASERCOAGULATION

FIELD OF THE INVENTION

This invention relates generally to the field of medicine, and more particularly, to a new medicinal drug-retinoprotector for treating intraocular hemorrhage, myopic chorioretinal dystrophies, congenital retinal dystrophies, retinal burns and prevention of injury in laser-coagulation.

A number of drugs used in the past have been known to speed up the absorption of extensive recurrent hemorrhages, for example fibrinolysin, urokinase, streptokinase, dycinone (ethamcelate), doxium, etc.

THE PRIOR ART

The antihemorrhagic agents heretofore routinely employed in the ophthalmological practice have produced either a purely angiotrophic impact (doxium) stabilizing the ocular microcirculation, or a hemostatic action (dycinone) useful in acute episodes of capillary hemorrhage, or a stimulating effect on the rheological properties of the blood (trental) resorted to in post-hemorrhagic changes of the retina, or a specifically thrombolytic effect (streptodecase, heparin).

However, none of the presently known agents is capable of a multiple action, first, stabilizing the ocular microvasculature (membranous structures of the vascular wall), second, affecting the anticoagulant and fibrinolytic properties of the blood, third, interfering with the destructive processes arising from increasingly rapid free-radical lipid oxidation both without and, especially, with concurrent light stimulation, in short an action encompassing the entire gamut of pathological changes attending hemorrhage.

SUMMARY OF THE INVENTION

It is the object of this invention to provide a new medicinal drug displaying low toxicity and a multidirectional antihemorrhagic action: stabilization of the membranous structures, protection of the membranous structures from intensive free-radical oxidation attending hemorrhage and other pathologies, disaggregation of the components forming the blood, restoration of normal oxygen utilization in the retina and reduction of the capillary permeability.

The drug of this invention represents a novel composition previously undisclosed in the literature. The retinoprotector for treating intraocular hemorrhage, myopic chorioretinal and congenital dystrophies, retinal burns and prevention of injury in lasercoagulation comprising an active substance and a pharmaceutical diluent, in accordance with this invention, the active substance being chlorohydrate 2-ethyl-6-methyl-3-hydroxypyridine hydrochloride having the following formula:

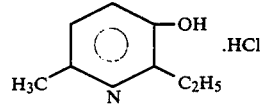

Preferably, the drug of this invention is employed in the form of a solution for injections and drops containing 1% of the active substance by weight.

The preferred pharmaceutical diluent for injection solutions is distilled water.

DETAILED DESCRIPTION OF THE INVENTION

Figure 4:
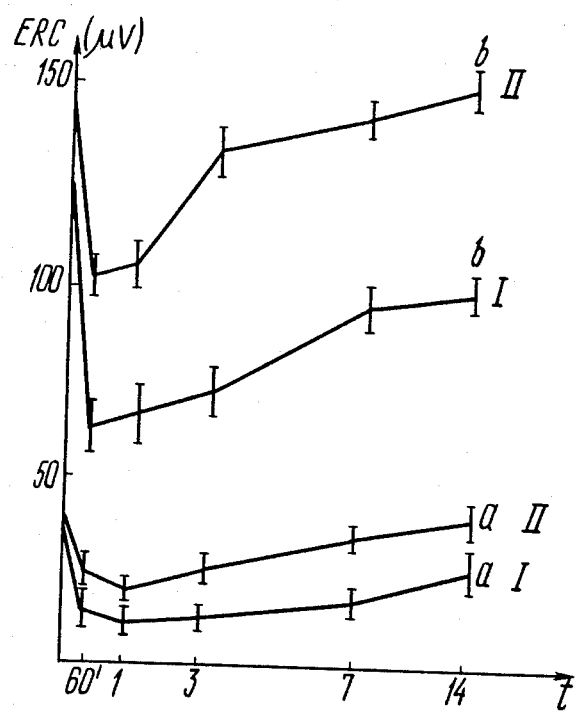

The drug of this invention, for convenience referred to as emoxypin, is recommended for therapeutic use in the following conditions:

1. The dry phase of central chorioretinal dystrophy (positively affects visual acuity).
2. Exudative-hemorrhagic phase of central chorioretinal dystrophy (partial absorption of hemorrhage, decreased area of neuroepithelium detachment, improved visual acuity).
3. Post-thrombotic retinal hemorrhage and lipid deposits in the central fundus (absorption of hemorrhagic areas, shrinking lipid deposits, improved visual acuity), subacute phase of thrombotic involvement in the central retinal vein and its branches 1.5 month and over subsequent to vascular collapse.
4. Myopic chorioretinal dystrophies:
a. dry phase, b. hemorrhagic phase, c. Fux's spot (absorption of hemorrhagic areas, improved visual acuity).
5. Hemophthalmia of various vascular etiology, history of onset, except diabetes related (partial absorption of hemophthalmia, improved visual acuity).

Sun burns of the retina, retinal burns incident to laser equipment operation (absorption of hemorrhagic areas, diminution of hemorrhagic and exudative activity, reduction of scotoma, improved visual acuity).

7. Central tapeto-retinal abiotrophies.
8. Vitreoretinal dystrophies.
9. Prevention of injury in lasercoagulation.

The drug of this invention is a retinoprotector exerting a beneficial action on the retina subject to stress, intense light, hyperoxia, intraocular hemorrhages. It is capable of restoring normal utilization of the retinal oxygen, increasing the content of cyclic nucleotides in the retina and other tissues, reducing capillary permeability, inducing thrombocyte disaggregation, lowering blood viscosity, slowing the rate of fibrin-monomer-fibrin polymer conversion, inhibiting thrombin formation, enhancing the fibrinolytic property of the blood, thereby contributing to intraocular hemorrhage absorption.

The retinoprotector of this invention was studied in animals and human subjects on a clinical basis.

Another study compared the drug of this invention with heparin combined with dexason as regards the efficacy of intraocular hemorrhage absorption.

Intraocular hemorrhage in rabbits was induced using an argon laser unit. Coagulation burns were made below the disc of the optic nerve using the beam power 200–400 mW, size 50–100μ, exposure time 0.1–0.2 s. The study comparing the therapeutic efficacy of the drug of this invention with that of a heparin and dexasone combination was done on 10 rabbits of the chinchilla line weighing 2.5–3 kg making up two groups of five animals each (10 eyes per group).

The therapy was initiated immediately following the onset of hemorrhage in the fundus. The drug of this invention was introduced in a dose of 0.5 ml of a 1% solution retrobulbarly for a period of 15 days in a single daily dosage. Heparin with dexasone (750 units heparin, 20 mg dexasone in one syringe) were injected retrobulbarly once daily for a length of 15 days.

5 days following the onset of hemorrhage, in the animals treated with the drug of this invention hemorrhagic absorption was significant, whereas in the group of animals on the heparin and dexasone schedule the extent of fundal hemorrhagic involvement remained virtually unchanged.

By the 14th day the animals treated with the drug of this invention showed complete absorption of the hemorrhage, whereas the animals receiving the combination of heparin and dexasone gave evidence of persistently extensive although actively absorbed hemorrhage which took 25–30 days to resolve completely.

It can thus be concluded that the drug of this invention, in contrast with the heparin and dexasone combination, is capable of speeding up the absorption of intraocular hemorrhage.

Yet another study compared the drug of this invention with dycinone with respect to the efficacy of intraocular hemorrhage absorption.

Intraocular hemorrhage in rabbits was induced using a laser unit. Coagulation burns were made below the disc of the optic nerve using the beam power 200–400 mW, size 50–100µ, exposure time 0.1–0.2 s. The study comparing the therapeutic efficacy of the drug of this invention with that of dycinone was done on 10 rabbits of the chinchilla line weighing 2.5–3 kg making up two groups of 5 animals each (10 eyes per group).

The therapy was initiated immediately following the onset of fundal hemorrhage. The drug of this invention was introduced in a dose of 0.5 ml of a 1% solution retrobulbarly for a period of 15 days in a single daily dosage. Dycinone was injected retrobulbarly in a dose of 0.5 ml of a 12.5% solution once daily for a length of 15 days.

5 days following the onset of hemorrhage, in the animals treated with the drug of this invention hemorrhagic absorption was significant, edemata contiguous to the coagulation burns subsided, whereas in the group of animals on dycinone the extent of fundal hemorrhagic involvement remained virtually identical to that seen one day following the development of hemorrhage.

By the 14th day the animals treated with the drug of this invention showed complete absorption of the hemorrhage, whereas the animals receiving dycinone gave evidence of persistently extensive hemorrhage which took 25–30 days to resolve completely.

It can thus be concluded that the drug of this invention, in contrast with dycinone, is capable of greatly speeding the absorption of intraocular laser-induced hemorrhage.

Still another study compared the drug of this invention with streptodecase with respect to the efficacy of intraocular hemorrhage absorption.

Intraocular hemorrhage in rabbits was induced using a laser unit. Coagulation burns were made below the disc of the optic nerve using the beam power 200–400 mW, size 50–100µ, exposure time 0.1–0.2 s. The study comparing the therapeutic efficacy of the drug of this invention with that of streptodecase was done on 10 rabbits of the chinchilla line weighing 2–3 kg making up two groups of 5 animals each (10 eyes per group).

The therapy was initiated immediately following the onset of experimental hemorrhage. The drug of this invention was introduced in a dose of 0.5 ml of a 1% solution retrobulbarly for a period of 15 days in a single daily dosage. Streptodecase was injected retrobulbarly in a dose of 0.5 ml 4 times starting from the day of hemorrhage onset every 2 days (10000 units per 1 ml).

5 days following the onset of hemorrhage, in the animals treated with the drug of this invention hemorrhagic absorption was significant, whereas in the group of animals of streptodecase the extent of hemorrhagic involvement remained virtually unchanged. It should, however, be pointed out that the animals on streptodecase developed a clear-cut allergic reaction to medication taking the form of extensive edema and rubescence affecting the lids and conjunctiva.

By the 14th day the animals treated with the drug of this invention showed complete absorption of the fundal hemorrhage. By the same time the animals on the streptodecase regimen gave evidence of considerable hemorrhagic involvement.

It can thus be concluded that the drug of this invention, in contrast with streptodecase, is capable of speeding the absorption of intraocular hemorrhage.

The therapeutic efficacy of the drug of this invention was likewise asessed in a controlled animal study of laser-induced intraocular hemorrhage.

Intraocular hemorrhage in rabbits was induced using an argon laser unit. Coagulation burns were made below the disc of the optic nerve using the beam power 200–400 mW, size 50–100µ, exposure time 0.1–0.2 s. Photographic pictures of the fundus were taken using a Retinophot unit. Animals were given the drug of this invention in a single daily dose (0.3–0.5 ml of a 1% solution) continued for a period of 15 days subconjunctivally or retrobulbarly. Electroretinogram (ERG) was traced on an ink writing encephalograph unit using a lens with a built-in electrode and a reference electrode (steel needle) which was introduced subcutaneously into the animal's cranium. Photic stimulation was provided by a flash bulb 0.3 J in power and lasting 50 ms. The original evoked response potential and the oscilloscope potential were recorded on tape off the oscilloscope screen. Effective energy consumption per flash was 180 J lasting 350 ms. The therapy in 40 animals (i.e. 80 eyes) was initiated immediately following the onset of laser-induced intraocular hemorrhage. There were two groups of control animals: the first received a placebo regimen (10 animals, 20 eyes), the second was medication free (20 animals, 40 eyes).

Both in the control and study animals immediately following the lasercoagulation and one day afterwards there were signs of periretinal and retinal hemorrhage adjacent to the coagulated fundal area and extending into the vitreous. The damage was less severe in the animals medicated with the drug of this invention. 7 days following the onset of hemorrhage, the animals in the study group showed significant absorption of the hemorrhage with complete subsidence of the edematous involvement. In the control animals the extent of hemorrhage was virtually unchanged with retinal blood effusion into the vitreous forming a partial hemophthalmus in some animals. By the 14th day following the onset of hemorrhage the animals in the study group exhibited complete absorption of the hemorrhage, whereas in the controls there was evidence of persistent retinal hemorrhage and partial hemophthalmus affecting the vitreous in some animals. Complete absorption of the hemorrhage in the control animals occurred over a period of 1.0–1.5 months.

Therefore, the drug of this invention is capable of a potent therapeutic action useful in the treatment of intraocular hemorrhage.

An electrophysiological examination in the control (untreated) and test (treated with the drug of this invention) groups of animals was made to evaluate the functional state of the retina in hemorrhage.

The results obtained from the electrophysiological study (electroretinogram) are illustrated in FIGS. 1 and 2 with relative amplitude of the a wave plotted on the ordinate (FIG. 1), and that of the b wave (FIG. 2) shown in percent of the original electroretinogram signal. Time elapsed following the onset of hemorrhage is plotted on the abscissa (origin—60 minutes, then 14 days at a one day interval). The curves designated as 1 in FIGS. 1 and 2 depict the results from the control group, while those designated as 2-the study group (treated with the drug).

The results of the electrophysiological examination showed that in the animals untreated with the drug of this invention (FIGS. 1 and 2, curves 1) the ERG signal was sharply suppressed. The a and b ERG waves in the animals on drug therapy (FIGS. 1 and 2, curved 2) returned to normal by the 10–15th day, while the amplitude of the a and b ERG waves in the non-medicated animals at the same stage in time was 37% and 42% of the control value, respectively. The ERG in the non-medicated animals took considerably longer time to return to normal in comparison to that of the treated animals with full restoration of the retinal electrical activity occurring over a period of 1.5–2 months.

The original evoked response potential ($R_2RRP$) in the untreated animals (FIG. 3A (I) was also significantly altered with its amplitude dropping to 60% of the norm by the 7th day following the onset of hemorrhage, while at the same time the $R_2RRP$ value in the rabbits treated with the drug (FIG. 3A (2)) had already reached the initial level. The oscilloscope potential value by the 7th day attained its control level in the treated animals (FIG. 3B) (2)), while the relative amplitude of this potential in the non-medicated animals (FIG. 3B (I)) was 60–70% of the control value. FIG. 3 (A,B) illustrates the recorded light stimulation.

Therefore, the drug of this invention is capable of preventing the emergence of intraocular hemorrhage related disturbances affecting the retinal function and biopotentials.

The drug of this invention, while acting to speed the absorption of recurrent intraocular hemorrhages, exerts a protective effect on the internal ocular structures against freshly caused hemorrhage.

The protective virtue of the drug of this invention employed in the post-operative period and following lasercoagulation was also assessed in an animal test.

Lasercoagulation was performed using an argon and krypton laser units. The coagulation burns were made below the disc of the optic nerve using the beam power 400 mW, size 200μ, exposure time 0.1–0.2 ms. Photographic pictures of the fundus were taken using a Retinophot unit. The total control and study population consisted of 60 animals (120 eyes, 60 eyes in each group).

The animals were put on a preventive schedule (one day and then 1 hour prior to lasercoagulation) and therapy with the drug of this invention in a dose of 0.5 ml of a 1% solution of the drug administered in a single daily dosage for a length of 10–15 days.

Both in the control (untreated) and test (treated) animals immediately following lasercoagulation and one day afterwards there were signs of edematous involvement adjacent to the coagulated fundal area which was more pronounced in the animals which did not receive the preventive therapy. In the animals treated with the drug of this invention prior to lasercoagulation fundal hemorrhage was induced with difficulty. One day following the coagulation there was no evidence of coagulation burns pigmentation detected either in the control or study groups of animals.

Subsequent ophthalmoscopy conducted in all the control animals demonstrated that the edemata surrounding the coagulation burns did not subside until the 7th day following the coagulation with coagulation burns pigmentation ensuing forthwith. It can be inferred from the ophthalmoscopy findings that the signs of thermal injury to the retina in animals untreated with the drug of this invention occurs by the 7–8th day subsequent to lasercoagulation.

The use of the drug of this invention is lasercoagulation greatly speeds the reparative changes in the retina incidental to laser therapy. Ophthalmoscopic examination of animals undergoing a preventive therapy with the drug demonstrated that the signs of edematous involvement in the area of the coagulation burns subside completely by the third day with latent coagulation burns pigmentation setting in at the same time. The ophthalmoscopic examination findings lead to the conclusion that in animals receiving the drug of this invention pigmentation of the retinal coagulation burns is completed by the 5th day as opposed to the 7–8th day in the controls, following lasercoagulation.

An electrophysiological examination in the control (untreated) and test (treated preventively) groups of animals was made to evaluate the functional state of the retinal in lasercoagulation. The results obtained from the electrophysiological study (ERG) are illustrated in FIG. 4 with the relative amplitudes of the a and b waves plotted on the ordinate in microvolts. The abscissa is used plot the time elasped after the onset of hemorrhage (origin—60 minutes, then 14 days at a one day interval). The results of the electrophysiological examination in FIG. 4 showed that in the animals on preventive and follow-up drug therapy the a and b waves returned to normal by the 10–15th day. By the same period of time the amplitude of the a and b (I) ERG waves in the non-medicated animals was only 60% of the control value.

It should be emphasized that the ERG in the non-medicated animals took considerably longer time to return to normal in comparison to that of the animals receiving a preventive and follow-up regimens with the drug of this invention. Full restoration of the ERG waves in the control animals (with no drug administration) occurred over a period of 1.5–2 months.

Therefore, the drug is capable of exerting a protective action in lasercoagulation, preserving the normal retinal function, speeding regenerative changes in the retina following lasercoagulation, and preventing retinal hemorrhage.

The therapeutic efficacy of the drug of this invention was studied in laser-induced retinal burns.

The experimental series was done on 20 rabbits of the chinchilla line weighing 3-3.5 kg. Laser burns were induced by means of an argon laser unit. The fundal burns were made below the disc of the animal's optic nerve using the beam power 600 mW, size 500μ, exposure time 0.1-0.2 s. Supervision of the subsequent development was carried out using indirect ophthalmoscopy and Retinophot photography. The control animals received no medication. The study group of animals received a therapeutic regimen consisting of the drug of this invention in a dose of 0.5 ml of a 1% solution injected retrobulbarly for a period of 7 days starting from obtainment of the retinal injury in the animal's eye. Immediately following the induction of retinal burns is both the control and study animals there were clearcut signs of edematous involvement in the affected fundal area with occasional small hemorrhages. One day after $E_z$ is the calibration pulse in mm.

Evaluation of the results (Table 1) suggests that intraocular hemorrhage gives rise to sharply decreased rheoophthalmographic amplitude so that as early as one hour following the onset of hemorrhage the rheographic factor $R_q$ falls to 50% of the control value. This slackening in the rheoophthalmogram is relatively stable in nature with the $R_q$ value showing no change even in 14 days after the onset of hemorrhage. Hemodynamics of the ocular vascular tract in rabbits takes a slow course toward restoration starting 2 weeks subsequent to the onset of hemorrhage so that after a lapse of 30 days the rheographic factor rises to as high as 56% of the control value. Complete normalization of the rheoophthalmogram usually occurs 1.0-1.5 months from the onset of hemorrhage. The results of the study are summarized in Table 1.

TABLE 1

| | | | Change in rheographic factor value in laser-induced intraocular hemorrhage | | | | | |
|---|---|---|---|---|---|---|---|---|
| Nos 1 | Rheographic factor value in % 2 | Number of experiments, n 3 | Control 4 | 1 hour following hemorrhage induction 5 | 24 hours following hemorrhage induction 6 | 3 days 7 | 7 days 8 | 14 days 9 | 30 days 10 |
| 1 | $R_q$ | 20 | 4.39 ± 0.26 | 2.19 ± 0.31 | 2.59 ± 0.42 | 2.63 ± 0.36 | 2.24 ± 0.17 | 2.17 ± 0.24 | 2.46 ± 0.38 | the burn induction in the study animals there was evidence of drastically diminished exudative activity completely subsiding by the 3-5th day with a pigmented scar forming in the burn site by the 5-7th day.

In the control group of animals (untreated) ophthalmoscopy done on the 1-3d day revealed signs of edema and limited hemorrhage. By the 5th day there was scattered diminution of the edematous involvement with incipient partial pigmentation of the coagulation burns. Full pigmentation of the coagulation burns in the control animals (untreated) occurred on the average by the 14th day.

In conclusion, it can be stated that the drug of this invention is a potent therapeutic agent useful in the treatment of laser-induced retinal burns.

Ocular hemodynamics was studied using the rheoophthalmography method in cases of laser-induced intraocular hemorrhage.

The intraocular hemorrhage in rabbits was induced using a laser unit. The coagulation burns were made below the disc of the optic nerve using the beam power 200-400 mW, size 50-100μ, exposure time 0.1-0.2 s. The fundus was photographed using a Retinophot unit. The animals were treated with a 1% solution (0.5 ml) of the drug of this invention starting on the day of hemorrhage onset once daily for the whole duration of therapy (15 days) administered retrobulbarly. Rheoophthalmography was performed by the L. A. Katsnelson method using a rheographic attachment secured to an electroencephalograph unit. The rheographic factor was computed using the following formula:

$$R_q = \frac{AE_w 1000}{E_z R}$$

where,
A is the pulse wave amplitude in mm;
$E_w$ is the calibration pulse in ohms;
R is the electrode resistance (impedance) in ohm.

A study of the therapeutic effect on the absorption of laser-induced intraocular hemorrhage compared a 1% solution of the drug of this invention with a 1% solution of vitamin $B_6$. Since vitamin $B_6$ is structurally analogous to the drug of this invention, it was judged expedient to compare their therapeutic effect. Two groups of animals were treated with a 1% solution of the drug of this invention (0.5 ml) and vitamin $B_6$ (1% solution 0.6 ml) starting from the initial day of hemorrhage once daily for the duration of therapy (15 days) administered in retrobulbar injections. The animals selected as controls were given a placebo regimen (0.5 ml No. 15). The subsequent results are listed in Table 2.

Evaluation of the hemodynamics of the ocular vascular tract in the animals on study further demonstrated that the rheoophthalmogram parameters obtained from the group on $B_6$ regimen are statistically authenticated and identical to those in both the untreated and placebo receiving groups of animals.

Ophthalmoscopy findings point to the fact that the therapy utilizing vitamin $B_6$ does not influence the rate of intraocular hemorrhage absorption. Complete absorption of the hemorrhage in this group of animals occurred by the 30-45th day in which they closely resembled the controls.

In response to therapy with the drug of this invention the duration of intraocular hemorrhage absorption was considerably shortened compared to the controls. Thus, on the 7th day from the onset of hemorrhage, in the animals treated with the drug of this invention there were signs of significant absorption of the fundal hemorrhage which was virtually completed by the 14th day, whereas in the control groups (untreated and on placebo program) and the group given vitamins $B_6$ there were still copious retinal and vitreous hemorrhages.

Rheographic indices variation in the group of animals treated with the drug noted 24 hours from the onset of hemorrhage was 82% of the initial value, whereas in the control group and the group receiving vitamin $B_6$ these indices were lowered—the rheographic factor $R_q$ was 59% and 61% of the initial control value, respectively. Restoration of the rheoophthalmogram in the animal group given the drug of this invention occurred by the 3-7th day, while in the control and vitamin $B_6$ groups the same improvement was observed only by the end of a 1-1.5 month period from the onset of hemorrhage.

Therefore, the experimental series illustrated that intraocular hemorrhage may unfavorably affect the ocular hemodynamics. The drug of this invention, in contrast to $B_6$, is capable of increasing the rate of intraocular hemorrhage absorption and exerting a restorative effect on the ocular hemodynamics.

An investigative effort was made to uncover the effect of the drug of this invention of retinal oxygenation and biopotentials. The study of the oxydation and bioelectrical processes occurring in the retina was conducted simultaneously with recording of the oxygen voltage (polarography) and biopotentials of the rabbit retina on a long-term experimental basis. For this purpose, a T-shaped platinum electrode 130 μm in diameter was introduced inside the rabbit eye through the sclera at the equator oculi by means of a microscrew. To accurately monitor the electrode accretion into the retina, the eyes enucleated from the animals upon completion of the study were subjected to histologic examination.

2. height (H)—maximal polarographic wave elevation for a given oxygen sample;

3. oxygen utilization rate in the retinal tissues—the tangent of the slope angle (tan α) formed by a line tangent to the sloping bend of the polarographic wave;

4. oxygen loss (h) following introduction of the drug of this invention computed as the ratio (h/H) 100%.

Figure 5:
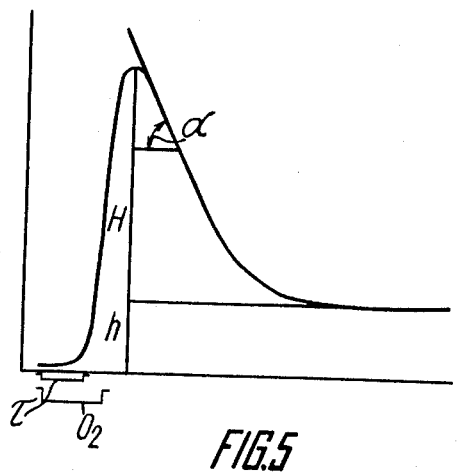

The polarogram is depicted in FIG. 5.

The time during which the oxygen sample remains effective is shown at the bottom of the polarogram.

ERG was recorded on an encephalograph unit from the electrode implanted into the retina and a reference electrode (steel needle) introduced into the animal's head subcutaneously. Light stimulation was provided by a Sonocle pulse stimulator using the flash power 0.3 J. The animals were put on a regimen utilizing the drug of this invention starting on the second day after the lasercoagulation in a dose of 0.63 mg/kg intravenously and retrobulbarly as well as 3-10 mg/kg administered intramuscularly in instillations of a 0.2% solution into the conjunctival sac.

The results of polarography in the control animals revealed that the drug of this invention slows the rate of oxygen utilization in the retina, the oxygen loss following the introduction of the drug of this invention falling into the range of between 16% and 42% (table 3). The

TABLE 2

Change in rheographic factor in laser-induced intraocular hemorrhage treated with the drug of this invention, vitamin $B_6$ and placebo

| Nos | Rheographic factor $R_q$ | Number of experiments, n | Control | 1 hour following hemorrhage induction | 24 hours following hemorrhage induction | 3 days | 7 days | 14 days | 30 days |
|---|---|---|---|---|---|---|---|---|---|
| 1 | 2 | 3 | 4 | 5 | 6 | 7 | 8 | 9 | 10 |
| 1 | Group treated with $B_6$ | 10 | 4.47 ± 0.34 | 2.25 ± 0.35 | 2.72 ± 0.51 | 2.55 ± 0.41 | 2.18 ± 0.43 | 2.21 ± 0.38 | 2.51 ± 0.47 |
| 2 | Group treated with the drug of this invention | 15 | 4.44 ± 0.17 | 2.44 ± 0.32 | 3.64 ± 0.48 | 4.26 ± 0.27 | 4.49 ± 0.36 | 4.48 ± 0.29 | 4.47 ± 0.41 |
| 3 | Control group (placebo) | 10 | 4.41 ± 0.28 | 2.38 ± 0.41 | 2.68 ± 0.46 | 2.61 ± 0.47 | 2.28 ± 0.25 | 2.32 ± 0.4 | 2.63 ± 0.51 |

The experimental findings were judged evaluable if the histological appearance of the rabbit eye section indicated that the wound opening penetrating the sclera and mucosa terminated at the retina, i.e., the end portion of the implanted electrode was actually abutting against the retina leaving it intact.

For polarographic analysis, the study used a platinum-iron couple with an internal galvanic circuit producing the oxygen half-wave potential equal to 0.6 V with the corresponding diffusion current proportional to the oxygen voltage. The results were recorded on an electron polarograph unit.

Brief controlled oxygen inhalations (in a standard environment) lasting 30 s served as oxygen test samples to qualitatively evaluate the retinal function.

The polarogram data were used to compute the following indices:

1. latent period (τ)—time from the start of oxygen supply until the start of polarogram elevation;

latent period duration and the polarogram amplitude did not change significantly in the majority of series (table 3). The peak of efficiency was observed 20-30 minutes following the administration of the drug. Judging by the study parameters, the drug remains effective for 1-1.5 hours after the introduction.

The electroretinographic findings are shown in Table 4. It will be noted that within 10-20 minutes in response to the introduction of the drug of this invention the a and b ERG wave amplitude showed a statistically authenticated increase from 28.2±4.8 μV to 48.4±8.5 μV (p<0.01) (70%) for the a wave, and from III±13.4μV to 144±13.6 μV (p<0.02) (30%) for the b wave.

To conclude, the findings obtained from ERG and polarography (simultaneously recorded) illustrate that despite the decreased oxygen utilization rate in the retina both the a and b ERG wave amplitudes increase following administration of the drug of this invention.

TABLE 3

Effect of the drug of this invention on oxygen utilization rate in rabbit retina

| Nos 1 | Drug 2 | Mode of administration and dosage 3 | Number of studies, n 4 | Prior to introduction Oxygen utilization rate (rel. un.) 5 | 10–60 minutes subsequent to introduction Oxygen utilization rate (rel. un.) 6 | P 7 | Oxygen loss 8 |
|---|---|---|---|---|---|---|---|
| 1 | Drug of the invention | intravenously 0.6 mg/kg | 6 | 0.93 ± 0.1 | 0.38 ± 0.02 | ≦0.01 | 16 ± 4.2 |
| 2 | Drug of the invention | intravenously 2–2.5 mg/kg | 5 | 0.88 ± 0.09 | 0.63 ± 0.08 | ≦0.01 | 42.3 ± 4.2 |

TABLE 4

Effect of the drug of this invention on rabbit ERG

| Nos 1 | Drug 2 | Mode of administration and dosage 3 | Number of studies, n 4 | Prior to introduction a ERG wave V 5 | Prior to introduction b ERG wave V 6 | Subsequent to introduction (10–60 minutes) a ERG wave V 7 | P 8 | Subsequent to introduction (10–60 minutes) b ERG wave V 9 | P 10 |
|---|---|---|---|---|---|---|---|---|---|
| 1 | Drug of this invention | intramuscularly, 4–8 mg/kg | 5 | 22.2 ± 4.8 | 111 ± 13.4 | 48.4 ± 8.5 | 0.01 | 144 ± 13.6 | 0.2 |
| 2 | Drug of this invention | intramuscularly, 10–15 mg/kg | 4 | 37.8 ± 1.9 | 146 ± 19.7 | 53.3 ± 3.3 | 0.02 | 163.6 ± 24.4 | 0.6 |

Figure 6:
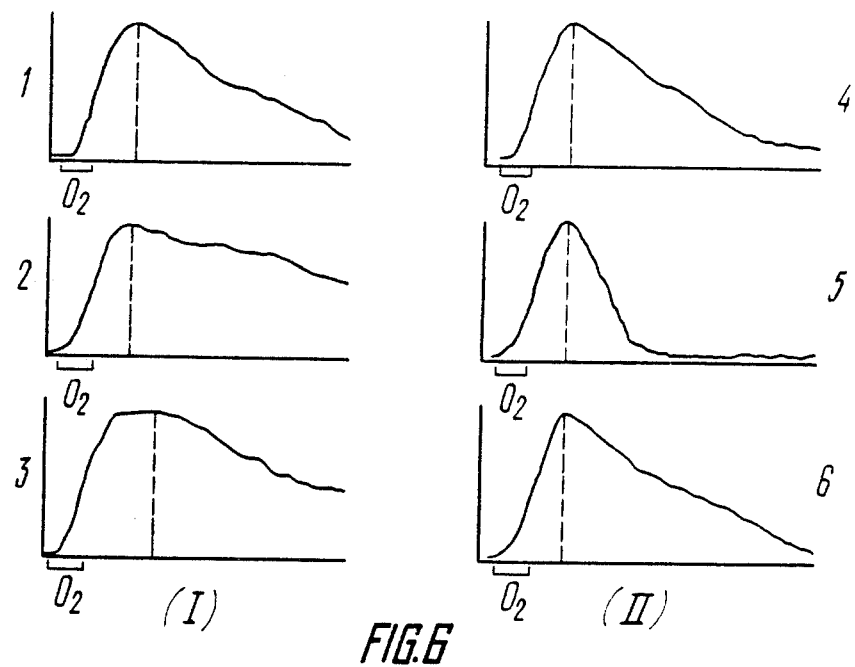

The effect of the drug of this invention on retinal oxygenation was studied in an experimentally induced intraocular hemorrhage caused by directly exposing the retinal vessels of the study animals to argon laser radiation. The coagulation burns were placed below the disc of the optic nerve using the beam power 500 mW, size 50–100μ, exposure time 0.1–0.2 s. FIG. 6 sums up the experimental findings from the study of oxygen utilization following administration of the drug to a healthy rabbit (I) and a rabbit affected with intraocular hemorrhage produced by means of an argon laser (II). The Figure likewise depicts the initial polarograms, where No. 1 designates the polarogram of the rabbit retina prior to introduction of the drug, No. 2—polarogram 15 min following the introduction of the drug, No. 3—55 min after the injection, No. 4—the polarogram of the rabbit retina prior to the onset of hemorrhage, No. 5—the polarogram of the rabbit retina one day from the onset of hemorrhage with no drug therapy, No. 6—the polarogram of the rabbit retina from the onset of hemorrhage modified by the drug therapy.

The findings from a number of studies indicated that lasercoagulation impairs oxygen utilization in the retina with the oxygen utilization rate one day after the lasercoagulation falling from 1.0 to 0.17 (a sixfold decrease compared to the controls) and the oxygen loss reaching 70%. By the 2–5th day from the lasercoagulation the retinal oxygen utilization was noted to return back to normal (results presented in Table 5).

TABLE 5

Effect of the drug of this invention on oxygen dynamics in the rabbit retina in experimental laser-induced hemorrhage

| Nos 1 | Time elapsed after lasercoagulation 2 | Drug 3 | Mode of administration 4 | Prior to administration Height of polarogram wave, mm 5 | Prior to administration Oxygen utilization rate (rel. units) 6 | Subsequent to administration Height of polarogram wave, mm 7 | Subsequent to administration Oxygen utilization rate (rel. units) 8 |
|---|---|---|---|---|---|---|---|
| 1 | 2 days | drug of this invention | intravenously 2 mg/kg | 90 | 1.25 | 95 | 1.1 |
| 2 | 5 days | — | intravenously 2 mg/kg | 124 | 1.9 | 132 | 2.4 |

The drug of this invention was found valuable in speeding the reparative change following lasercoagulation (normalization of oxygen utilization).

It thus becomes apparent that the drug of this invention has a substantial influence on the retinal oxygenation and bioelectrical activity, alleviates the retinal response to lasercoagulation, stimulates the retinal function.

The drug of this invention was subjected to a clinical trial contemplating the following objectives:

1. clinical assessment of the new agent's efficacy
2. therapeutic efficacy evaluation in comparison to other agents employed in ophthalmology.

The drug of this invention was used in the treatment of the following conditions:
1. Central chorioretinal dystrophies:
   a. the dry phase of central chorioretinal dystrophy
   b. exudative-hemorrhagic phase of central chorioretinal dystrophy.
2. Thromboses of the central retinal vein and its branches:
   a. post-thrombotic retinal hemorrhage
   b. lipid deposits in the central fundus.
3. Hemophthalmia of various vascular etiology:
   a. diabetes mellitus
   b. angiitis
   c. thrombosis with neovascularization
   d. central chorioretinal dystrophies.
4. Myopic chorioretinal dystrophies:
   a. dry phase
   b. hemorrhagic phase
   c. Fux's spot.
5. Central tapeto-retinal abiotrophies
6. Sun and laser induced retinal burns
7. Vitreochorioretinal dystrophies:
   a. juvenile X-chromosome retinoschisis
   b. dystrophic myopic retinoschisis.

A clinical trial of the drug of this invention was conducted in 380 patients with a total of 453 eyes, all showing signs of chronic involvement. Prior to the initiation of therapy with the drug the subjects were given an angioprotector regimen utilizing such agents as dycinone, doxium, various absorption promoting medication, lydase and chemotrypsin injected intramuscularly, fibrinolysin, leukosim subconjunctivally, physiotherapy which proved ineffective with respect to absoprtion of the retinal and vitreous hemorrhage, persistently low visual acuity associated with dystrophic changes in the central fundus.

The clinical experience with the drug of this invention demonstrated its efficacy in promoting the absorption of retina and vitreous located hemorrhage. The drug was employed in ocular conditions of varying vascular etiology such as vitreous hemorrhage, subacute phase of thrombotic involvement in the central retinal vein and its branches, myopia related hemorrhage, exudative-hemorrhagic phase of central chorioretinal dystrophy. The efficacy of the drug was evaluated in the dry phase of chorioretinal dystrophy and dry phase of myopic chorioidosis, juvenile X-chromosome and dystrophic retinoschisis as well as remote postoperative period (1-1.5 years) following surgery for dystrophic retinal detachment to improve the visual function. The drug of this invention was used in the treatment of retinal burns associated with sun radiation laser equipment operation. The results from the clinical trial were evaluated according to a set of subjective and objective criteria related to the documented visual acuity, visual field, ophthalmoscopic features (diminution of the extent of retinal hemorrhage and neuroepithelium detachment), electrophysiological findings. Fluorescein angiography and fundus photography was performed in some cases. Improvement was defined when ophthalmoscopy consistently pointed to a positive change with an obligatory increase in visual acuity. If no increase in visual acuity and visual field was noted, the response could not be evaluated as improvement.

Kuhnt-Unius dystrophies were referred to the group of central chorioretinal dystrophies commonly showing signs of bilateral involvement in subjects aged 40-80 years. 10.3% of patients were affected with hypertension, in 58.3% hypertension was compounded by atherosclerosis, 14.6% presented with generalized atherosclerosis. The drug was employed in 175 eyes with central chorioretinal dystrophies of varying etiology. For the clinical trial the subjects were broken down into 2 groups. The first group consisted of the eyes with the dry phase of central chorioretinal dystrophy manifested as defects of the pigment epithelium or localized pigment epithelium detachment. The second group consisted of the eyes presenting with neuroepithelium detachment of a serous nature or serous-hemorrhagic neuroepithelium detachment, i.e., the exudative-hemorrhagic phase of Kuhnt-Unius dystrophy. Table 6 presents the findings obtained from the therapy using the drug of this invention in the dry phase of central chorioretinal dystrophy.

TABLE 6

Change in visual acuity in the dry phase of central chorioretinal dystrophy treated with the drug of this invention

| Number of eyes | Improvement increased VA by | | | No effect |
|---|---|---|---|---|
| | 0.1 | 0.2 | 0.3 | |
| 22 | 5 | 6 | 2 | 9 |

The clinical picture in that stage of disease showed no change. An increase of visual acuity by 0.2-0.3 in 36.4% testifies to the efficacy of the drug of this invention at this stage of disease. Wide-ranging clinical experience with trental similarly administered in the form of retrobulbar injections in 67 patients failed to produce a single instance of a 0.3 increase in visual acuity. Electrophysiological examination performed in 40 patients prior to and following the completion of therapy using the drug of this invention revealed substantial improvement as regards the retinal function.

In the second group with the exudative-hemorrhagic phase of central chorioretinal dystrophy the drug of this invention was given to a total of 153 eyes. All the patients were previously treated with agents such as anginin and micleron orally, locally and as subconjunctival or retrobulbar injections of dycinone or a combination of dycinone and dexason (12.5% dycinone in a dose of 0.3-0.5 ml, 750 units dexason in a dose of 0.1-0.2 ml plus a 12.5% solution of dycinone in a dose of 0.3-0.5 ml mixed in a single syringe). The therapy failed to favorably affect the extent of neuroepithelium detachment or exudative-hemorrhagic neuroepithelium detachment. Table 7 shows the results of employing the drug of this invention versus the combination of dexason and dycinone in exudative-hemorrhagic phase of central chorioretinal dystrophy.

TABLE 7

Visual acuity variation in exudative-hemorrhagic phase of central chorioretinal dystrophy treated with the drug of this invention

| Drug | Number of eyes | Response to therapy | |
|---|---|---|---|
| | | Improvement | No effect |
| Drug of this invention | 153 | 123 (81.5%) | 30 (18.5%) |
| Dexason plus dycinone | 58 | 28 (48.8%) | 30 (51.8%) |

After a course of retrobulbar injections 123 of 153 eyes responded with favorable change in the fundus and an increase in visual acuity averaging 0.08-0.1, while the corresponding average following the dexason and dycinone combination regimen was 0.03.

Table 8 presents the findings from electrophysiological examination of the patients with the exudative-hemorrhagic phase of central chorioretinal dystrophy. As seen from table 8, the amplitudes of the a and b ERG waves by 38% and 24%, respectively, above the initial level in response to a course of the drug of this invention.

TABLE 8

Change in relative amplitude of the ERG waves in patients with central chorioretinal dystrophies in response to therapy with the drug of this invention

| | Number of eyes | Prior to therapy ERG a wave | ($\mu$V) b wave | Subsequent to therapy ERG a wave | ($\mu$V) b wave |
|---|---|---|---|---|---|
| Central chorioretinal dystrophies | 40 | 45.75 ± 2.23 | 185.8 ± 4.92 | 63.4 ± 2.1 38% | 230.8 ± 6.21 24% |

Therapy with the drug of this invention resulted in shrinkage of the neuroepithelium detachment and increased visual acuity in 81.5% of patients. Such an increase in visual acuity indicates the high efficacy of the drug of this invention in this severe impairment of the central fundus. A comparative efficacy analysis of the drug of this invention versus the combination of dexason and dycinone showed the former to be far superior since the use of dexason and dycinone in combination drug therapy elicited a 48.8% positive response rate. What follows is an excerpt from the case history of Patient T., 83 years old, with diagnosed cicatricial phase of central chorioretinal dystrophy, adduced by way of example. Prior to the start of therapy visual acuity in the right eye was counting fingers 40 cm away from the patient's face, left eye—counting fingers at 20 cm from the face. Following a course of therapy (1% solution of the drug of this invention in a dose of 0.5 ml, given retrobulbarly, No. 15) visual acuity in the right eye rose to 0.03, left eye to 0.02. The duration of response was documented at 3 months after which visual acuity reverted to the initial level. An injection course using trental (0.5 ml, No. 15, given retrobulbarly) failed to produce a visually identifiable response. A repeated course of therapy with the drug of this invention (1% solution of the drug in a dose of 0.5 ml given retrobulbarly, No. 15) resulted in an increase in visual acuity in the right eye up to 0.01, left eye up to 0.03.

Therefore, increase of the residual vision in the cicatrical phase of central chorioretinal dystrophy in response to the therapy with the drug of this invention substantiates the experimental findings concerning the beneficial effect on the retinal metabolic processes.

The drug of this invention was employed in the treatment of retinal hemorrhage and secondary lipid deposition in the central fundus and in 138 eyes with signs of thrombosis involving the central retinal vein and its branches in the subacute phase 1.5 month and longer from the onset of disease. In the acute phase of disease the patients were usually given angioprotector agents, carbonic anhydrase derived drugs, retrobulbar injection of heparin combined with dexason, subconjunctival injections of fibrinolysin. The therapy failed to completely reverse the thrombotic condition with large residual areas of retinal hemorrhage which rendered subsequent lasercoagulation impossible. Table 9 lists the results of using the drug of this invention, dycinone, heparin and dexason in combination in the treatment of post-thrombotic retinal hemorrhage.

TABLE 9

Results of treating post-thrombotic retinal hemorrhage with the drug of this invention, dycinone, and the heparin and dexason combination

| Drug | Number of eyes | Response Improvement | No effect |
|---|---|---|---|
| Drug of this invention | 138 | 101(73.1%) | 37(26.9%) |
| Dycinone | 45 | 20(44.5%) | 25(55.5%) |
| Heparin plus dexason | 42 | 17(36.9%) | 25(63.1%) |

Increased visual acuity and diminution of the retinal hemorrhage was documented in 101 eyes (73.1%) following a course of therapy with the drug of this invention (1% solution of the drug in a dose of 0.5 ml given retrobulbarly, No. 15), whereas the regimens utilizing dycinone and the combination of heparin and dexason gave the response rates of 45.9% and 30%, respectively. The average increase in visual acuity following the therapy with the drug of this invention was 0.2, whereas this variable in the dycinone and heparin plus dexason combination schedules was 0.06 and 0.07, respectively.

Table 10 shows the results of functional evaluation of the retina in patients with thromboses affecting the central retinal vein. As seen from the table, the relative amplitudes of the a and b ERG waves increase by 34% and 16%, respectively (above the starting value) in response to a course of therapy with the drug of this invention.

TABLE 10

Change in amplitude of ERG waves in patients with thromboses affecting the central retinal vein and its branches responding to treatment with the drug of this invention

| | Number of eyes affected | Prior to therapy ERG ($\mu$V) a wave | b wave | Subsequent to therapy ERG ($\mu$V) a wave | b wave |
|---|---|---|---|---|---|
| Thromboses | 24 | 46.1 ± 2.85 | 206.1 ± 5.71 | 61.7 ± 2.34 34% | 239.5 ± 5.81 16% |

Therefore, the clinical and electrophysiological findings from the study of the drug of this invention illustrate its high efficacy in the subacute phase of thromboses affecting the central retinal vein and its branches.

10 patients with thromboses of the central retinal vein were ophthalmoscopically shown to have small quantities of a hard exudate matter (lipids) in the central fundus which was the immediate cause of the decrease in visual acuity. Following a course of therapy with the drug of this invention ophthalmoscopic examination revealed regression in the extent of the lipid deposits in the central fundus with a concomitant increase in visual acuity by 0.2 on the average. The clinical findings serve as corroboration of the effect exerted by the drug of this invention on lipid metabolism. A clinical study established the high efficacy of the drug of this invention in the treatment of hemophthalmia. Table 11 summarizes the results of treating recurrent hemophthalmia with the drug of this invention in 70 eyes.

TABLE 11

Results of treating recurrent hemophthalmia with the drug of this invention

| Condition | Number of eyes | Response Improvement | No effect |
|---|---|---|---|
| Diabetes mellitus | 28 | 20 | 8 |
| Ils's disease, angiites | 14 | 13 | 1 |
| Thromboses with neovascularization | 25 | 24 | 1 |
| Central chorioretinal dystrohies | 3 | 3 | — |
| Total | 70 | 60(85.7%) | 10(14.3%) |

As can be seen from Table 11, the hemophthalmia stemmed from severe impairment of the ocular vasculature: proliferative phase of diabetic retinopathy, Ils's disease or juvenile hemorrhage into the vitreous body, neovascularization of the retina secondary to thromboses affecting the branches of the central retinal vein which were not coagulated in time. Vitreous hemorrhages in this group of patients had a tendency to recur. Prior to therapy with the drug of this invention the patients received fibrinolysin in subconjunctival injections and retrobulbarly administered dycinone. The therapy failed to elicit an increase in visual acuity. Improved clinical appearance (partial absorption of the hemophthalmus) and increased visual acuity observed in 85.7% of the eyes with recurrent hemophthalmia treated with the drug testifies to the high efficacy of the drug of this invention in this form of severe pathology affecting the ocular vasculature.

In hemophthalmia with underlying diabetes mellitus the average increase in visual acuity was 0.06 fluctuating between 0.03 and 0.2. The increase in visual acuity in patients with recurrent hemophthalmia arising secondary to thromboses affecting branches of the central retinal vein was on the average 0.2. In the group of patients with angiitis visual acuity increased by 0.12 on the average, while that documented in the group with central chorioretinal dystrophies was 0.23. Table 12 presents the results of therapy with the drug of this invention and dycinone in hemophthalmia of vascular etiology.

TABLE 12

Results of therapy with the drug of this invention and dycinone in hemophthalmia of vascular etiology

| Drug | Number of eyes | Response Improvement | No effect |
|---|---|---|---|
| Drug of this invention | 70 | 60(85.7%) | 10(14.3%) |
| Dycinone | 42 | 17(40.4%) | 25(59.6%) |

The increase in visual acuity in hemophthalmia treated with dycione was 0.02 on the average.

Therefore, the findings obtained from the clinical study showed the drug of this invention to be superior to other agents conventionally employed in clinical ophthalmology to combat hemophthalmia of varying vascular etiology.

The efficacy of the drug of this invention was the subject of a clinical trial in 44 eyes with myopia of high and moderate degree associated with decreasing visual acuity due to localized damage to the central fundus. 20 of 44 eyes had signs of the dry phase of dystrophy resembling myopic chorioidosis and in 22 eyes the condition had progressed into the hemorrhagic phase (13 of which number had an underlying Fux's spot). The drug of this invention proved highly effective in this group of severely ill subjects. In the dry phase of disease with no concomitant change in the clinical picture visual acuity was noted to rise by an average of 0.2 in 15 of 20 eyes (75%). To adduce an example, patient T., 52 years old, presented with progressive myopia in both eyes (18 diopters) dated to childhood. The patient previously received cycles of vitamin and tissue therapy repeated regularly on a twice yearly basis. Following a course of therapy with the drug of this invention (1% solution of the drug in a dose of 0.5 ml, retrobulbarly, No. 15) visual acuity in the right eye rose from 0.2 to 0.4, in the left eye from 0.1 to 0.4. Electrophysiological examination showed barely traceable a ERG wave prior to therapy with the amplitude rising to 25–30 $\mu$ V following its completion, b ERG wave prior to therapy was 75 $\mu$ V, following the completion of the course 220–225 $\mu$ V (right eye). ERG examination in the left eye demonstrated that the a wave was barely traceable prior to therapy with its amplitude rising to 12.5 $\mu$ V following. The b ERG wave amplitude prior to therapy was 100 $\mu$ V rising upon completion of a course with the drug of this invention to 160–175 $\mu$ V. A repeated course of therapy with the drug of this invention resulted in visual acuity increasing to 0.6–0.8 in the right eye and to 0.6 in the fellow eye.

In the hemorrhagic phase of disease there were positive shifts in the clinical appearance, partial absorption of hemorrhage, and increased visual acuity observed in 10 of 22 eyes. To adduce an example, patient M., 35 years old, presented with myopia of high degree, fresh retinal hemorrhage in the central fundus, corrected visual acuity was 0.1 in both eyes. Following a course with the drug of this invention (1% solution of the drug in a dose of 0.5 ml, retrobulbarly, No. 15) there was partial absorption of the retinal hemorrhage with corrected visual acuity increasing to 0.2 in the right eye and to 0.4 in the left eye.

Therefore, it can be concluded that the drug of this invention is of high therapeutic efficacy in cases of severe fundal pathology associated with myopic chorioretinal dysttrophies.

A clinical trial of the drug of this invention was also conducted in 11 patients (22 eyes with signs of Starhardt's disease). Table 13 shows the findings with respect to the effect of the drug of this invention on visual acuity and visual field in response to treatment of Starhardt's disease.

TABLE 13

Change in visual acuity and visual field in Starhardt's disease

| Phase of disease | Number of eyes | VA increase in VA 0.07-0.08 | VA 0.1-0.2 | No response | Visual field Improvement | No effect |
|---|---|---|---|---|---|---|
| 1 | 2 | 3 | 4 | 5 | 6 | 7 |
| I-II phase | 2 | — | — | 2 | — | 2 | — |
| II-III phase | 16 | 2 | 4 | 4 | 6 | 10 | 6 |
| III-IV phase | 4 | 2 | — | — | 2 | 3 | 1 |
| Total | 22 | 4 | 4 | 6 | 8 | 15 | 7 |

The most significant finding made in this group of patients is the increase in visual acuity in 20 of 22 eyes and diminution of the central scotoma in 13 of 20 eyes in the II–IV phase of disease commonly resisting therapy. A comparative evaluation of the therapeutic efficacy in Starhardt's disease with a regimen using the drug of this invention versus the previously known agent flavinat showed the former to be superior.

The therapy with the drug of this invention (1% solution of the drug in a dose of 0.5 ml given retrobulbarly, No. 15) was started in 5 patients (7 eyes) with sun induced burns of the macular area arising in consequence of observing a solar eclipse without protective spectacles. The subjects were aged 16 to 35 years with the onset of damage dated 2-3 months. At referral the complaint included lowered visual acuity and a central scotoma in the affected eye 10×10°. Visual acuity was decreased down to 0.8 in 5 eyes. The visual field in the subjects on study showed centrally located absolute scotomata. Following a course of therapy with the drug of this invention visual acuity in 5 eyes rose from 0.8 to 1.0, in 2 eyes from 0.5 to 0.6. In all the eyes the absolute scotomatous area diminished to 2×3°. The clinical picture was unchanged.

Therapy with the drug of this invention was administered to 3 patients (3 eyes) with laser-induced burns of the macular area incident to work with the laser equipment. The onset of injury was 2 days. The fundal area of the burn was marked by retinal hemorrhage and edema affecting the neuroepithelium. Visual acuity in 2 cases fell to 0.3, in another case to 0.1–0.2. The visual field contained an absolute scotoma 5×10°. Following the therapy with the drug of this invention visual acuity in 2 eyes returned to 1.0, the hemorrhage and edema resolved completely. In one of the eyes (that sustained large-area affection, where the focus of hemorrhage and edema took one area of the disc), visual acuity remained the same, pre-retinal hemorrhage was fully absorbed, and a dense pigmented area resembling a scar formed in the central fundus.

Therefore, the drug of this invention is capable of a highly potent therapeutic effect useful in the treatment of laser and sun induced retinal burns with a complete response rate of 80% observed by the end of therepy. When other therapeutic modalities are employed, visual acuity is fully regained in 15–30% of laser induced retinal burns noted 1.5–2 months from the start of therapy. It can be concluded from the above-stated that the drug of this invention is highly beneficial in the treatment of retinal burns of varying etiology.

The drug of this invention is a retinoprotector exerting a beneficial action on the retina subject to stress, intense light, hyperoxia, intraocular hemorrhages. Clinical and experimental studies of the composition have demonstrated that the drug has a wide range of properties promoting rapid absorption of the intraocular hemorrhages, inhibition of exudative activity, diminution of the extent of neuroepithelium detachment and lipid deposition, restoration of the visual function. Evaluation of the data from the study of the drug's mechanism of action indicate that it has an inhibitory influence on lipid oxydation induced by hemoglobin, strengthens the membranous structures of the blood cells (erythrocytes), suppresses aggregation of the blood forming components (thrombocytes), slows the rate of fibrin-monomer-to-fibrin-polymer conversion (antipolymerizing effect), enhances fibrinolytic activity of the blood, stimulates rheological properties of the blood, exerts a vasoactive action in intraocular hemorrhage and effectively competes with phosphodiesterase of the cyclic nucleotides.

The broad spectrum of therapeutic action exhibited by the drug of this invention renders it applicable in the treatment of intraocular hemorrhage of varying etiology, chorioretinal and congential dystrophies, retinal burns, and prevention of injury in lasercoagulation.

The active substance of the drug of this invention is substantially a finely crystallized white odourless powder, slightly sour to taste, readily soluble in water and alcohol, poorly soluble in ether and acetone, remaining stable at high temperatures (up to 200° C.).

The drug of this invention can be prepared by conventional techniques in various therapeutic forms (such as eye drops, injections, tablets). Preferably, the drug of this invention is used in the form of subconjunctival or retrobulbar injections. For therapeutic purposes the drug of this invention is administered subconjunctivally in a dose of 0.3 ml of a 1% solution once daily for a length of 10–15 days or, alternatively, in retrobulbar injections in a dose of 0.5 ml of a 1% solution once daily for a length of 10–15 days.

To protect the retina from the injurious effect of coherent radiation in lasercoagulation, the drug is introduced retrobulbarly in a dose of 0.5 ml of a 1% solution one day prior to lasercoagulation and then repeated I hour preceding the treatment. As a follow-up regimen, the drug is given for a length of 2–3 days in retrobulbar injections utilizing the same dosage (0.5 ml of 1% solution) once daily.

There are no side effects and contraindications to the use of the drug. The drug of this invention should be stored in a place protected from light. List B.

We claim:

1. A retinoprotector for treating intraocular hemmorrhage, myopic chorioretinal dystrophies, congenital retinal dystrophies and retinal burns and prevention of injury in lasercoagulation comprising a retinoprotective effective amount of 2-ethyl-6-methyl-3-hydroxypyridine hydrochloride and a pharmaceutical vehicle.

2. An injectable form of the retinoprotector of claim 1 containing 1% of 2-ethyl-6-methyl-3-hydroxypyridine hydrochloride by weight.

3. The retinoprotector of claims 1 or 2, wherein said pharmaceutical vehicle is distilled water.

4. A method for protecting the retina from injury from exposure to light and for treating intraocular hemorrhage, myopic chorioretinal dystrophies, congenital retinal dystrophies and retinal burns comprising administering to the subject a retinoprotective effective amount of 2-ethyl-6-methyl-3-hydroxypyridine hydrochloride.

5. The method of claim 4 wherein the 2-ethyl-6-methyl-3-hydroxypyridine hydrochloride is administered by injection as a solution in distilled water.

6. The method of claim 5 wherein the solution in distilled water contains about 1% by weight of 2-ethyl-6-methyl-3-hydroxypyridine hydrochloride.

* * * * *